US012722013B2

(12) United States Patent
Bjanes et al.

(10) Patent No.: US 12,722,013 B2
(45) Date of Patent: Sep. 1, 2026

(54) SYSTEM AND METHOD FOR DELIVERING SENSORY FEEDBACK TO THE CORTEX VIA ELECTRICAL STIMULATION

(71) Applicant: University of Washington, Seattle, WA (US)

(72) Inventors: David Bjanes, Seattle, WA (US); Chet T. Moritz, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 584 days.

(21) Appl. No.: 17/090,685

(22) Filed: Nov. 5, 2020

(65) Prior Publication Data

US 2021/0138251 A1 May 13, 2021

Related U.S. Application Data

(60) Provisional application No. 62/933,147, filed on Nov. 8, 2019.

(51) Int. Cl.

| | |
|---|---|
| ***A61N 1/00*** | (2006.01) |
| ***A61N 1/05*** | (2006.01) |
| ***A61N 1/36*** | (2006.01) |

(52) U.S. Cl.

CPC ....... *A61N 1/36175* (2013.01); *A61N 1/0529* (2013.01); *A61N 1/0551* (2013.01); (Continued)

(58) Field of Classification Search

CPC .............. A61N 1/36062; A61N 1/0529; A61N 1/36178; A61N 1/36175; A61N 1/0551; A61N 1/36171; A61N 1/36057

See application file for complete search history.

(56) References Cited

U.S. PATENT DOCUMENTS

| | | | |
|---|---|---|---|
| 7,302,296 | B1 | 11/2007 | Hoffer |
| 8,090,446 | B2 | 1/2012 | Fowler |

(Continued)

FOREIGN PATENT DOCUMENTS

| | | | | |
|---|---|---|---|---|
| CA | 3006219 A1 * | 10/2007 | .......... | A61N 1/0551 |
| CN | 102436302 | 5/2012 | | |

(Continued)

OTHER PUBLICATIONS

E. M. Schmidt, M. J. Bak, F. T. Hambrecht, C. V. Kufta, D. K. O'Rourke, and P. Vallabhanath, "Feasibility of a visual prosthesis for the blind basedon intracortical micro stimulation of the visual cortex," Brain, vol. 119, No. 2, pp. 507-522, 1996.

(Continued)

*Primary Examiner* — Sana Sahand

(74) *Attorney, Agent, or Firm* — Christensen O'Connor Johnson Kindness PLLC

(57) ABSTRACT

Systems and methods for delivering sensory feedback to the cortex via electrical stimulation are disclosed herein. In one embodiment, the system includes: an implant electrically coupled to a brain, a spinal cord or peripheral nerves of the user through implant electrodes. The implant is configured to deliver electrical stimulus through the implant electrodes. The system also includes a computing device that performs actions including: delivering the electrical stimulus via the implant electrodes; and generating neural signals that are evoked by the electrical stimulus. The neural signals correspond to information transferred to the brain, spinal cord or peripheral nerves through the implant electrodes. The electrical stimulus is encoded as a combination of at least two parameters selected from a group of parameters consisting of a frequency, a pulse-width, an amplitude, a number of pulses in a train, and a train interval.

19 Claims, 12 Drawing Sheets

(52) U.S. Cl.
CPC ..... *A61N 1/36062* (2017.08); *A61N 1/36171* (2013.01); *A61N 1/36178* (2013.01)

(56) References Cited

U.S. PATENT DOCUMENTS

| | | | | |
|---|---|---|---|---|
| 9,549,704 | B1 | 1/2017 | Buerger | |
| 2006/0161218 | A1* | 7/2006 | Danilov | A61B 5/682 607/45 |
| 2010/0168606 | A1* | 7/2010 | Edwards | A61B 3/0033 600/558 |
| 2010/0274320 | A1* | 10/2010 | Torgerson | A61N 1/36167 607/59 |
| 2011/0307079 | A1 | 12/2011 | Oweiss | |
| 2017/0113056 | A1 | 4/2017 | Stocco | |
| 2018/0185649 | A1 | 7/2018 | Michaeli | |
| 2020/0061378 | A1 | 2/2020 | Ganguly | |
| 2021/0236821 | A1* | 8/2021 | Sinclair | A61B 5/4848 |

FOREIGN PATENT DOCUMENTS

| | | | | |
|---|---|---|---|---|
| CN | 104951082 | | 9/2015 | |
| CN | 106250633 | | 12/2016 | |
| CN | 106650793 | | 5/2017 | |
| CN | 110719797 | | 1/2020 | |
| EP | 2868343 | A1 * | 5/2015 | A61B 5/04001 |
| EP | 3363495 | A1 * | 8/2018 | A61N 1/0551 |
| KR | 101641581 | | 7/2016 | |
| KR | 20190050094 | | 5/2019 | |
| NZ | 337392 | | 6/2002 | |
| WO | 2019122905 | | 6/2019 | |
| WO | 2020124838 | | 6/2020 | |

OTHER PUBLICATIONS

E. Zrenner, "Will retinal implants restore vision?" Science, vol. 295,No. 5557, pp. 1022-1025, Feb. 2002.

Panetsos, F., et al., "Consistent phosphenes generated by electrical microstimulation of the visual thalamus, An experimental approach for thalamic visual neuroprostheses," Frontiers Neuroscience, vol. 5, p. 84, Jul. 2011.

Pezaris, J.S., and R.C., Reid, "Demonstration of artificial visual percepts generated through thalamic microstimulation," Proc. Nat. Acad. Sci. USA, vol. 104, No. 18, pp. 7670-7675, May 2007.

P. M. Lewis et al., "Advances in implantable bionic devices for blindness:A review," Anz J. Surg., vol. 86, No. 9, pp. 654-659, Sep. 2016.

D. B. Grayden and G. M. Clark, "Implant design and development,"in Cochlear Implants, Practical Guide, 2nd ed. New York, NY, USA: Wiley, 2006, pp. 1-20.

R. K. Shepherd and D. B. McCreery, "Basis of electrical stimulation of the cochlea and the cochlear nucleus," Adv. Otorhinolaryngol., vol. 64, pp. 186-205, 2006.

D. S. Lee et al., "Cross-modal plasticity and cochlear implants," Nature, vol. 409, No. 6817, pp. 149-150, Jan. 2001.

E. A. Schafer, "Experiments on the electrical excitation of the cerebral cortex in the monkey," Brain, vol. 11, pp. 1-6, 1888.

E. J. Tehovnik, "Electrical stimulation of neural tissue to evoke behavioral responses," J. Neurosci. Methods, vol. 65, No. 1, pp. 1-17, Mar. 1996.

R. Romo, A. Hernández, A. Zainos, and E. Salinas, "Somatosensory discrimination based on cortical microstimulation," Nature, vol. 392, pp. 387-390, Mar. 1998.

S. Ohara, N. Weiss, and F. A. Lenz, "Microstimulation in the region of the human thalamic principal somatic sensory nucleus evokes sensations like those of mechanical stimulation and movement," J. Neurophysiol., vol. 91, No. 2, pp. 736-745, Mar. 2004.

B. M. London, L. R. Jordan, C. R. Jackson, and L. E. Miller, "Electrical stimulation of the proprioceptive cortex (area 3a) used to instruct a behaving monkey," IEEE Trans. Neural Syst. Rehabil. Eng., vol. 16, No. 1, pp. 32-36, Feb. 2008.

A. R. Houweling and M. Brecht, "Behavioural report of single neuron stimulation in somatosensory cortex," Nature, vol. 451, No. 7174, pp. 8-65, Jan. 2008.

S. Venkatraman and J. M. Carmena, "Behavioral modulation of stimulusevoked oscillations in barrel cortex of alert rats," Frontiers Integrative Neurosci., vol. 3, pp. 1-10, Jun. 2009.

S. Kim, T. Callier, G. A. Tabot, R. A. Gaunt, F. V. Tenore, and S. J. Bensmaia, "Behavioral assessment of sensitivity to intracortical microstimulation of primate somatosensory cortex," Proc. Nat. Acad. Sci. USA, vol. 112, No. 49, pp. 15202-15207, Dec. 2015.

J. E. O'Doherty et al., "Active tactile exploration using a brain-machine-brain interface," Nature, vol. 479, No. 7372, pp. 228-231, Nov. 2011.

J. Berg et al., "Behavioral demonstration of a somatosensory neuroprosthesis," IEEE Trans. Neural Syst. Rehabil. Eng., vol. 21, No. 3, pp. 500-507, May 2013.

E. E. Thomson, R. Carra, and M. A. L. Nicolelis, "Perceiving invisible light through a somatosensory cortical prosthesis," Nature Commun., vol. 4, Jan. 2013, Art. No. 1482.

S. N. Flesher et al., "Intracortical microstimulation of human somatosensory cortex," Sci. Transl. Med., vol. 8, No. 361, p. 141, Oct. 2016.

P. R. Kennedy and R. A. E. Bakay, "Restoration of neural output from a paralyzed patient by a direct brain connection," Neuroreport, vol. 9, No. 8, pp. 1707-1711, Jun. 1998.

M. A. L. Nicolelis and M. A. Lebedev, "Principles of neural ensemble physiology underlying the operation of brain-machine interfaces," Nature Rev. Neurosci., vol. 10, No. 7, pp. 530-540, Jul. 2009.

E. E. Fetz, "Operant conditioning of cortical unit activity," Science, vol. 163, No. 3870, pp. 955-958, Feb. 1969.

L. R. Hochberg et al., "Neuronal ensemble control of prosthetic devices by a human with tetraplegia," Nature, vol. 442, No. 7099, pp. 164-171, Jul. 2006.

M. D. Serruya, N. G. Hatsopoulos, L. Paninski, M. R. Fellows, and J. P. Donoghue, "Instant neural control of a movement signal," Nature, vol. 416, No. 6877, pp. 141-142, Mar. 2002.

D. M. Taylor, S. I. H. Tillery, and A. B. Schwartz, "Direct cortical control of 3D neuroprosthetic devices," Science, vol. 296, No. 5574, pp. 1829-1832, Jun. 2002.

S. Musallam, B. D. Corneil, B. Greger, H. Scherberger, and R. A. Andersen, "Cognitive control signals for neural prosthetics," Science, vol. 305, No. 5681, pp. 258-262, Jul. 2004.

J. Wessberg et al., "Real-time prediction of hand trajectory by ensembles of cortical neurons in primates," Nature, vol. 408, No. 1, pp. 361-365, 2000.

M. Velliste, S. Perel, M. C. Spalding, A. S. Whitford, and A. B. Schwartz, "Cortical control of a prosthetic arm for self-feeding," Nature, vol. 453, No. 7198, pp. 1098-1101, Jun. 2008.

G. Santhanam, S. I. Ryu, B. M. Yu, A. Afshar, and K. V. Shenoy, "A high-performance brain-computer interface," Nature, vol. 442, No. 7099, pp. 195-198, Jul. 2006.

J. Viventi et al., "Flexible, foldable, actively multiplexed, high-density electrode array for mapping brain activity in vivo," Nature Neurosci., vol. 14, No. 12, pp. 1599-1605, Dec. 2011.

G. Schalk, D. J. McFarland, T. Hinterberger, N. Birbaumer, and J. R. Wolpaw, "BCI2000: A general-purpose brain-computer interface (BCI) system," IEEE Trans. Biomed. Eng., vol. 51, No. 6, pp. 1034-1043, Jun. 2004.

M. S. Johannes, J. D. Bigelow, J. M. Burck, S. D. Harshbarger, M. Van Kozlowski, and T. Van Doren, "An overview of the developmental process for the modular prosthetic limb," Johns Hopkins APL Tech. Dig., vol. 30, No. 3, pp. 207-216, 2011.

L. Resnik, S. L. Klinger, and K. Etter, "The DEKA arm: Its features, functionality, and evolution during the veterans affairs study to optimize the DEKA arm," Prosthetics Orthotics Int., vol. 38, No. 6, pp. 492-504, 2014.

L. R. Hochberg et al., "Reach and grasp by people with tetraplegia using a neurally controlled robotic arm," Nature, vol. 485, No. 7398, pp. 372-375, May 2012.

(56) References Cited

OTHER PUBLICATIONS

C. Klaes, Y. Shi, S. Kellis, J. Minxha, B. Revechkis, and R. A. Andersen, "A cognitive neuroprosthetic that uses cortical stimulation for somatosensory feedback," J. Neural Eng., vol. 11, No. 5, Oct. 2014, Art. No. 056024.
S. J. Bensmaia and L. E. Miller, "Restoring sensorimotor function through intracortical interfaces: Progress and looming challenges," Nature Rev. Neurosci., vol. 15, No. 5, pp. 313-325, May 2014.
D. J. Weber, R. Friesen, and L. E. Miller, "Interfacing the somatosensory system to restore touch and proprioception: Essential considerations," J. Motor Behav., vol. 44, No. 6, pp. 403-418, Jan. 2012.
S. Kim et al., "A computational model that predicts behavioral sensitivity to intracortical microstimulation," J. Neural Eng., vol. 14, No. 1, 2017, Art. No. 016012.
G. A. Tabot et al., "Restoring the sense of touch with a prosthetic hand through a brain interface," Proc. Nat. Acad. Sci. USA, vol. 110, No. 45, pp. 18279-18284, Nov. 2013.
C.-M. Scheff, "Experimental model for the study of changes in the organization of human sensory information processing through the design and testing of non-invasive prosthetic devices for sensory impaired people," ACM SIGCAPH Comput. Phys. Handicapped, No. 36, pp. 3-10, 1986. [Online]. Available: https://dl.acm.org/citation.cfm?id=15713.
M. A. Salas et al., "Proprioceptive and cutaneous sensations in humans elicited by intracortical microstimulation," Elife, vol. 7, Apr. 2018, Art. No. e32904. doi: 10.7554/eLife.32904.
M. C. Dadarlat, J. E. O'Doherty, and P. N. Sabes, "A learning-based approach to artificial sensory feedback leads to optimal integration," Nature Neurosci., vol. 18, No. 1, pp. 138-144, 2015.
J. A. Cronin et al., "Task-specific somatosensory feedback via cortical stimulation in humans," IEEE Trans. Haptics, vol. 9, No. 4, pp. 515-522, Oct./Dec. 2016.
G. Y. Fridman, H. T. Blair, A. P. Blaisdell, and J. W. Judy, "Perceived intensity of somatosensory cortical electrical stimulation," Exp. Brain Res., pp. 499-515, 2010.
E. L. Mackevicius, M. D. Best, H. P. Saal, and S. J. Bensmaia, "Millisecond precision spike timing shapes tactile perception," J. Neurosci., vol. 32, No. 44, pp. 15309-15317, Oct. 2012.
A. I. Weber et al., "Spatial and temporal codes mediate the tactile perception of natural textures," Proc. Nat. Acad. Sci. USA, vol. 110, No. 42, pp. 17107-17112, Oct. 2013.
R. Romo, A. Hernández, A. Zainos, C. D. Brody, and L. Lemus, "Sensing without touching: Psychophysical performance based on cortical microstimulation," Neuron, vol. 26, No. 1, pp. 273-278, 2000.
D. A. Bjånes and C. T. Moritz, "Automated center-out rodent behavioral trainer (ACRoBaT), an automateddevice for training rats to perform a modified center out task," Behavioural Brain Res., vol. 346, pp. 115-121, Jul. 2018.
R. Efron, "The minimum duration of a perception," Neuropsychologia, vol. 8, No. 1, pp. 57-63, 1970.
N. A. Fitzsimmons, W. Drake, T. L. Hanson, M. A. Lebedev, and M. A. L. Nicolelis, "Primate reaching cued by multichannel spatiotemporal cortical microstimulation," J. Neurosci., vol. 27, No. 21, pp. 5593-5602, May 2007.
R. V. Shannon, "A model of safe levels for electrical stimulation," IEEE Trans. Biomed. Eng., vol. 39, No. 4, pp. 424-426, Apr. 1992.
D. R. Merrill, M. Bikson, and J. G. R. Jefferys, "Electrical stimulation of excitable tissue: Design of efficacious and safe protocols," J. Neurosci. Methods, vol. 141, No. 2, pp. 171-198, 2005.
A. T. Rajan et al., "The effects of chronic intracortical microstimulation on neural tissue and fine motor behavior," J. Neural Eng., vol. 12, No. 6, 2015, Art. No. 066018.
A. Hernandez, A. Zainos, and R. Romo, "Neuronal correlates of sensory discrimination in the somatosensory cortex," Proc. Nat. Acad. Sci. USA, vol. 97, No. 11, pp. 6191-6196, 2000.
J. P. Herman and S. J. Watson, "The Rat Brain in Stereotaxic Coordinates (2nd edn)", Trends in Neurosciences, vol. 10 issue 10, 1987, p. 439.
Formento, et al., "Electrical Spinal Cord Stimulation Must Preserve Proprioception to Enable Locomotion in Humans with Spinal Cord Injury." Nature Neuroscience, vol. 21, pp. 1728-1741, 2018.
Collinger, et al., "7 Degree-of-freedom Neuroprosthetic Control by an Individual with Tetraplegia," Lancet, 381, pp. 557-564, 2013.
Earley, et al., "Joint Speed Discrimination and Augmentation for Prosthesis Feedback," 2018.
Hu, et al., "NRI: Towards Restoring Natural Sensation of Hand Amputees via Wearable Surface Grid," NSF Award Search: Award # 1637892, <https://www.nsf.gov/awardsearch/showAward?AWD_ID=1637892&HistoricalAwards=false> [Retrieved Mar. 29, 2021], 4 pages.
Valle, et al., "Biomimetic Intraneural Sensory Feedback Enhances Sensation Naturalness, Tactile Sensitivity, and Manual Dexterity in a Bidirectional Prosthesis," Neuron 100, pp. 37-45, Oct. 10, 2018.
Lee, et al., "Engineering Artificial Somatosensation Through Cortical Stimulation in Humans," Frontiers in System Neuroscience, vol. 12, Article 24, Jun. 2018.
Valle, et al., "Comparison of linear frequency and amplitude modulation for intraneural sensory feedback in bidirectional hand prostheses," Scientific Reports, pp. 1-13, 2018.
Graczyk, et al., "The Neural Basis of Perceived Intensity in Natural and Artificial Touch," Science Translational Medicine, Research Article, Neurotechnology, Oct. 26, 2016.
Liu, et al., "Reduce Brain Computer Interface Inefficiency by Combining Sensory Motor Rhythm and Movement-related Cortical Potential Features," J. Neural Eng. 17 (2020).
Bjånes, et al., "Development of a Robust Encoding Scheme for Delivering Artificial Sensory Information through an ICMS Electrical Interface," University of Washington, 2018.
Bjånes, et al., "A Robust Encoding Scheme for Delivering Artificial Sensory Information via Direct Brain Stimulation," IEEE Transactions on Neural Systems and Rehabilitation Engineering, pp. 1-10, 2019.
Liu, et al., "A Wireless Neuroprosthetic for Augmenting Perception Through Modulated Electrical Stimulation of Somatosensory Cortex," IEEE, 2017.
Marzullo, et al.,"Development of Closed-Loop Neural Interface Technology in a Rat Model: Combining Motor Cortex Operant Conditioning With Visual Cortex Microstimulation," IEEE Trans Neural Syst Rehabil Eng., 2010, 18(2): 117-126.
Pham, et al., "An Auditory Brain-Computer Interface Based on the Self-Regulation of Slow Cortical Potentials," The American Society of Neurorehabilitation, Neurorehabilitation and Neural Repair 19(3), pp. 206-218, 2005.
Konrad, et al., "Implantable Brain Computer Interface: Challenges to Neurotechnology Translation," Neurobiology of Disease 38, pp. 369-375, 2010.
Vato, et al., "Shaping the Dynamics of a Bidirectional Neural Interface," PLoS Computational Biology, Jul. 2012, vol. 8, Issue 7, pp. 1-15.
Piech, et al., "Stimdust: A Mm-Scale Implantable Wireless Precision Neural Stimulator with Ultrasonic Power and Communication," 2018.
Shin, et al., "Evoked haptic sensations in the hand via noninvasive proximal nerve stimulation," J. Neural Eng. 15 (2018).
Santhanam, et al., "A High-Performance Brain-Computer Interface," Nature Publishing Group, vol. 442, pp. 195-198, 2006.
Tan, et al., "A Neural Interface Provides Long-Term Stable Natural Touch Perception," Neuroprosthetics, vol. 6, Issue 257, 2014.
Greenwald, et al., "Bidirectional Neural Interfaces: Applications and VLSI Circuit Implementations," Med Biol Eng Comput, 2017.

* cited by examiner

SYSTEM AND METHOD FOR DELIVERING SENSORY FEEDBACK TO THE CORTEX VIA ELECTRICAL STIMULATION

CROSS-REFERENCE TO RELATED APPLICATION

This application claims the benefit of U.S. Provisional Application No. 62/933,147, filed Nov. 8, 2019, the disclosure of which is expressly incorporated herein by reference in its entirety.

STATEMENT OF GOVERNMENT LICENSE RIGHTS

This invention was made with Government support under Grant No. EEC1028725, awarded by the National Science Foundation. The Government has certain rights in the invention.

BACKGROUND

Cortical neuroprostheses offers a tool to improve health and function via direct communication with the brain. Cortical stimulation is explored for its promise to convey visual, auditory, and somatosensory information. In order for such stimulation to faithfully deliver high-bandwidth information to the brain, it is necessary to understand how to reliably encode information within the stimulation signals.

Although early studies demonstrated somatosensory approaches, recent advances in neural recording and decoding have largely outpaced progress in sensory feedback. Current brain computer interfaces (BCIs) encode neuronal activity, enabling subjects to complete a variety of tasks. Recent improvements have been achieved to incorporate higher channel counts in BCIs and machine learning algorithms to control biomimetic robotic arms in real-time. As a result, human BCI users can control 7-10 degrees of freedom. These open-loop controllers, however, rely on slow visual feedback pathways and may realize greater improvements by incorporating a closed-loop sensory feedback.

Achieving coordinated, dexterous control using a BCI may require a short-latency, high-fidelity feedback signal. However, the optimal design of this signal is the topic of much debate. Biomimetic signal designers have delivered electrical stimulation patterns similar to the neural signals expected by the sensory cortex. By recording neural activation patterns of a sensation elicited via mechanical stimuli, electrical stimulation mimicking those recorded patterns can evoke similar sensations, which at times may be indistinguishable from natural sensation. This technique is useful for verifying the quality of the elicited sensory percepts; unfortunately, it excludes typical BCI users, whom no longer receive natural sensory input to their brain due to spinal cord injury or stroke.

In some other approaches, sensory substitution relies on the plasticity of the brain to “substitute” an incoming artificial signal for a physical sensation. This approach presents stimulation first and measures the evoked sensation afterwards. By exploiting cortical adaptation, electrical stimulation can artificially evoke a variety of sensations that are utilized by rodents, primates, and human patients to solve sensorimotor tasks.

Conventional technology encodes the stimulus using a fixed frequency or two different frequencies. These conventional technologies determined that discrimination was possible at low frequencies (<44 Hz), but temporal resolution was poor. Later work found discrimination between two discrete frequency patterns possible, but this required changing several other parameters to control for consistent pulse delivery over the specified time period. Accordingly, systems and methods for an effective, high-bandwidth delivery of electrical stimulus to the neural system are needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In an embodiment, a system for delivering information to a user includes: an implant electrically coupled to a brain, a spinal cord or peripheral nerves of the user through implant electrodes, where the implant is configured to deliver electrical stimulus through the implant electrodes. The system also includes a computing device having a non-transitory computer-readable medium, wherein the computer-readable medium includes computer-executable instructions stored thereon which, in response to execution by at least one processor of the computing device, cause the computing device to perform actions including: delivering the electrical stimulus via the implant electrodes; and generating neural signals that are evoked by the electrical stimulus. The neural signals correspond to information transferred to the brain, spinal cord or peripheral nerves through the implant electrodes. The electrical stimulus is encoded as a combination of at least two parameters selected from a group of parameters consisting of a frequency, a pulse-width, an amplitude, a number of pulses in a train, and a train interval.

In one embodiment, the at least two parameters are the pulse-width and the amplitude of the electrical stimulus. In another embodiment, the combination of the pulse-width and the amplitude of the electrical stimulus produces a variable charge-per-pulse (CPP) as the pulse-width and the amplitude of the electrical stimulus vary. In one embodiment, the at least two parameters further include the frequency.

In one embodiment, the frequency is within a range of 1-400 Hz.

In another embodiment, the amplitude is less than 120 μA.

In one embodiment, the pulse-width is within a range of 50-500 μs.

In another embodiment, the number of pulses in a train is within a range of 1-20 pulses per train, and the train interval is within a range of 50-500 ms.

In an embodiment, a method for stimulating a user includes: delivering an electrical stimulus via electrodes connecting an implant to a brain, a spinal cord, or peripheral nerves of the user; and based on delivering the electrical stimulus, evoking neural signals in a brain, spinal cord, or peripheral nerves of the user. The electrical stimulus encodes the neural signals via a combination of a pulse-width and an amplitude of the electrical stimulus.

In one embodiment, the neural signals correspond to information transferred to the user.

In another embodiment, the method also includes measuring information delivered to the user.

In one embodiment, the amplitude and the pulse width of the combination vary to modulate the neural signal. In another embodiment, the amplitude of the combination remains constant and the pulse-width of the combination changes to modulate the neural signal. In another embodiment, the pulse-width of the combination remains constant and the amplitude of the combination changes to modulate the neural signal.

In an embodiment, a method for delivering electrical stimulus through an implant having implantable electrodes coupled to a brain, or a spinal cord, or peripheral nerves of a user includes: delivering the electrical stimulus to the user via the implantable electrodes, where the electrical stimulus is encoded as a combination of at least two parameters selected from a group consisting of a frequency, a pulse-width, an amplitude, a number of pulses in a train, or a train interval. The method also includes, based on delivering the electrical stimulus, evoking neural signals in the brain, the spinal cord, or the peripheral nerves of the user.

In one embodiment, the method also includes assigning individual weighting function to the at least two parameters. In one embodiment, the at least two parameters are the pulse-width and the amplitude.

In another embodiment, changes in the pulse-width and the amplitude result in a variable charge-per-pulse (CPP) delivered to the user.

In one embodiment, the combination of the at least two parameters includes a first combination of the pulse-width and the amplitude sent to the user in a first stimulus train, and a second combination of the pulse-width and the amplitude sent to the user in a second stimulus train. The first combination is different from the second combination. The first stimulus train is separated from the second stimulus train by a time gap that is shorter than 100 ms.

In one embodiment, the time gap is shorter than 50 ms.

In one embodiment, the combination of the at least two parameters includes a first combination of the pulse-width and the amplitude sent to the user in a first stimulus train, and a second combination of the pulse-width and the amplitude sent to the user in a second stimulus train. The first combination is different from the second combination, and the first stimulus train is separated from the second stimulus train by a time gap that is shorter than a 50% of the first stimulus train.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

The inventive technology is directed to utilizing effective cortical stimulation pattern to deliver high-resolution sensory feedback via electrical stimulation to the cortex or other parts of the neural system (e.g., spine). In some embodiments, the signal parameters of a stimulation pattern are amplitude, pulse-width, frequency, number of pulses, and train interval. By modulating these parameters, intra-cortical micro-stimulation (ICMS) can convey information (also referred to as "sensory information") delivered to primary sensory cortex. In some embodiments, signal parameters (also referred to as "neural signal parameters") are based on changes in amplitude and pulse-width of the stimulation pulses. In combination, the signal amplitude and pulse-width modulate the amount of electrical charge of the delivered stimulation pulses (charge-per-pulse or CPP). In many embodiments, the combination of the signal amplitude and pulse-width results in a relatively high signal sensitivity by the cortex of test animal.

With the understanding of the parameters of the cortical signal (neural signal) that animals can detect in an artificial electrical stimulation pattern, encoding models can be selected to maximize resolution of an input signal, with the goal of delivering high bandwidth information directly to the brain or a spinal cord or peripheral nerves of the animal. In some embodiments, a combination of signal amplitude and pulse-width can be used to modulate intensity of the signal delivered to the cortex, which results in modulated sensitivity of the test subject to the signal pattern. In some embodiments, modulating the combination of signal amplitude and pulse-width (i.e., modulating CPP) reliably encodes information via direct electrical cortical stimulation of the subject. In some embodiments, the changes in the signal amplitude and pulse-width can be controlled such that the electrical charge (i.e., area under the curve or CPP) changes or remains constant or close to constant. For example, as the signal amplitude is increased, the pulse-width may be proportionally decreased, and vice versa to maintain a relatively constant sensitivity to stimulation signals. In other embodiments, increasing both the signal amplitude and the pulse-width results in an improved sensitivity to the stimulation pattern.

In some embodiments, the inventive technology relies on certain frequency thresholds for delivering stimulation pulses. For example, the operating frequency may be kept below 400 Hz.

Figure 1:
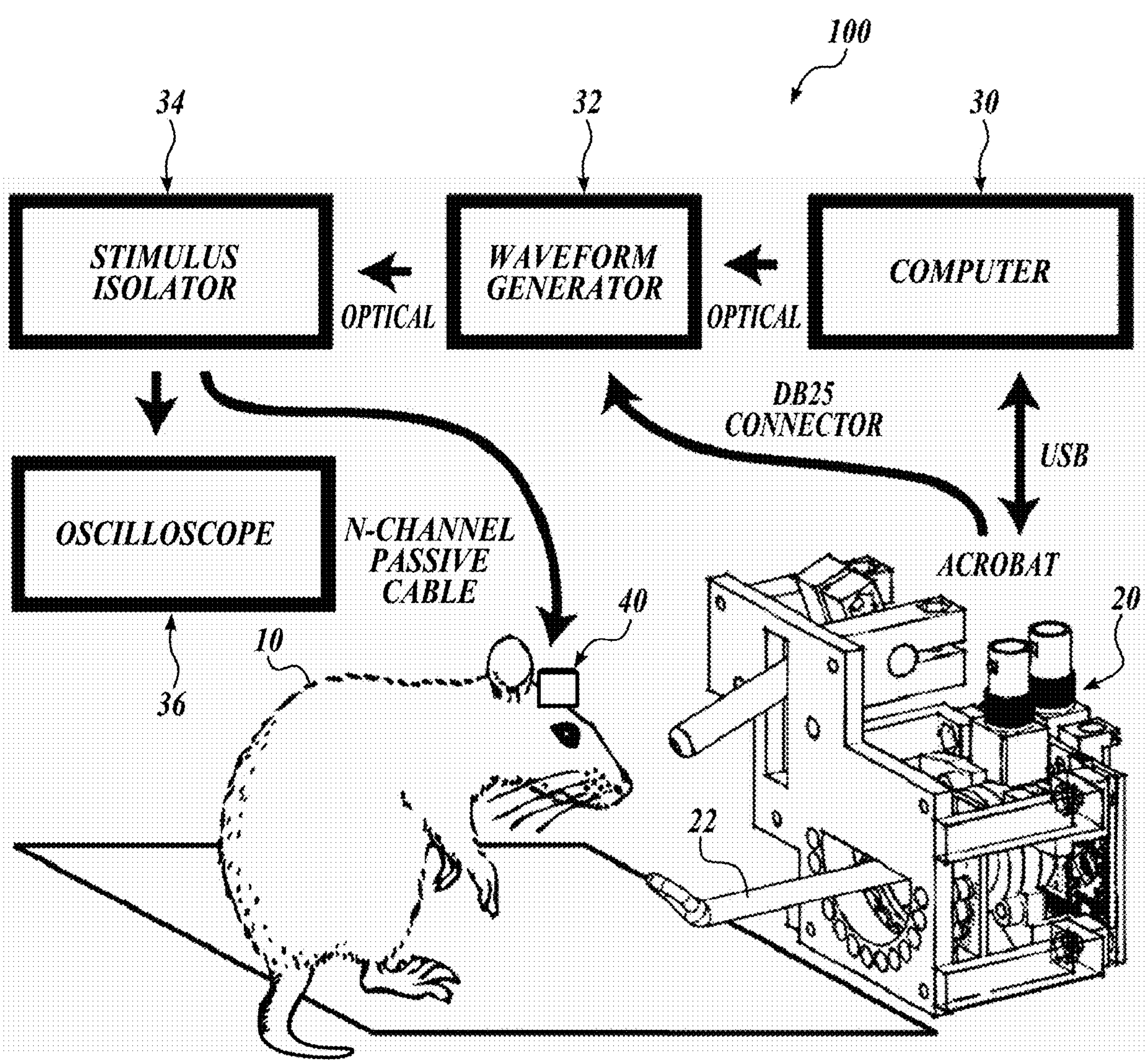
FIG. 1 is a schematic diagram illustrating delivery of the stimulus in accordance with an embodiment of the present technology.

FIG. 1 is a schematic diagram illustrating delivery of the stimulus in accordance with an embodiment of the present technology. In different tests, adult female Long-Evans rats (Charles River, 200-300 g) were trained to perform a modified center-out task. Animals were housed 1-3 per cage during initial training. The housing room light cycle was set to a 12-hour day/night cycle, shifted such that the housing and behavior room was dark from 9 AM to 9 PM. This permitted training/testing to take place during the animals' active, dark cycle. Ad libitum access to food was allowed throughout the training, but animals were restricted from water in their home cages. Free water was given for ½ hour each day after their training/testing sessions. For correctly completing a trial during the behavioral task sessions, drops of apple juice were administered as a liquid reward (0.05 ml).

Each test animal (rat) 10 followed a 16-step protocol developed to train rats to perform the modified center-out task as follows. Using a 3D printed joystick, rats explored three targets within the workspace. A light cue illuminated when the rat entered the desired target, while no light cue was presented when the rat was exploring non-desired targets. Subjects received a liquid reward for dwelling 1.25 s in the illuminated target. If a rat dwelled for 1.25 s in a non-desired target, a timeout penalty of 5 s was assessed.

Animals completing over 200 trials per session with above 75% success rate were deemed proficient at the task. They were then implanted with cortical implant 40 having stimulating electrodes 42. Thereafter, direct cortical electrical stimulation replaced the light cue.

In some embodiments, a behavioral data collection system 100 included the ACRoBaT training system 20, having a 3-position manipulator 22, a desktop computer 30, and a wavefront generator (e.g., a benchtop stimulator by Tucker Davis Technologies). The ACRoBaT training system 20 integrated data from several sources, synchronized timing variables, and outputted stimulation parameters in real time. The desktop computer 30 logged behavioral variables and sent session parameters to ACRoBaT's onboard microprocessor through USB connection. The waveform generator 32 received real-time stimulation parameters via a custom serial protocol from the ACRoBaT system. In different embodiments, different connection protocols may be used between the ACRoBaT system 20 and other elements of the system 100. In some embodiments, a passive cable (e.g., a 16-channel cable) connected the stimulus isolator 34 (e.g., TST MS16) to the implanted array 40 on the animals' head. The animal 10 was capable of freely moving around the arena. The signals sent from the stimulus isolator 34 were observable on an oscilloscope 36. Measuring the signals also enables measuring information delivered to the user.

Figures 2A, 2B:
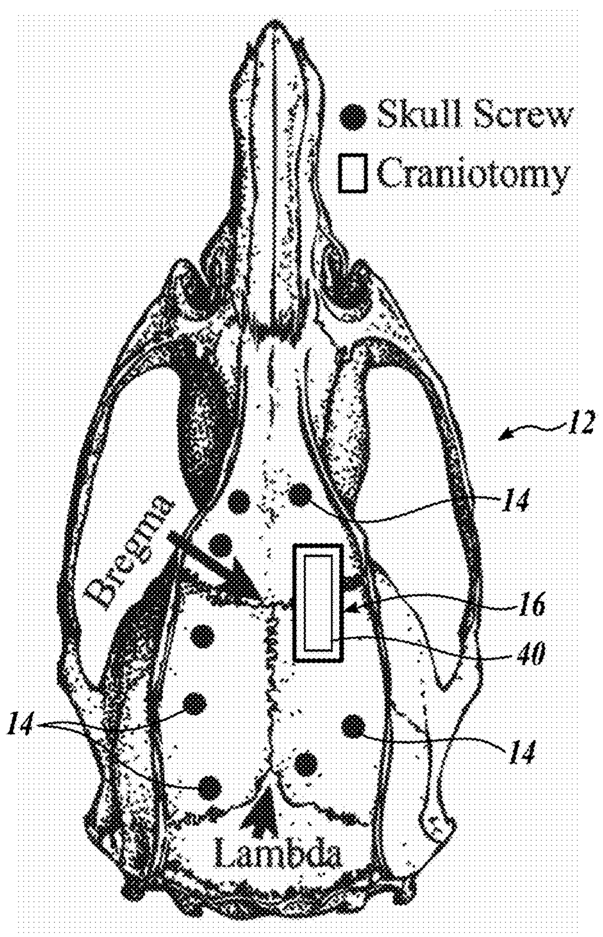
FIG. 2A illustrates placement of an implant for delivery of the stimulus in accordance with an embodiment of the present technology.
FIG. 2B illustrates details of implant placement in accordance with an embodiment of the present technology.
Figure 2C:
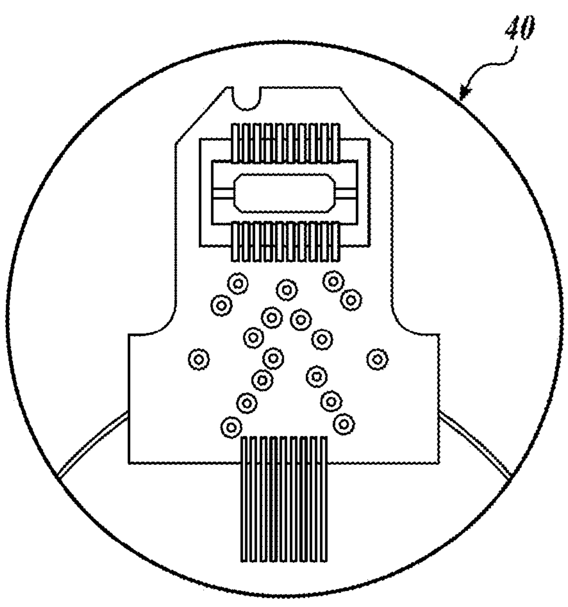
FIG. 2C illustrates an implant for delivery of the stimulus in accordance with an embodiment of the present technology.
Figure 2D:
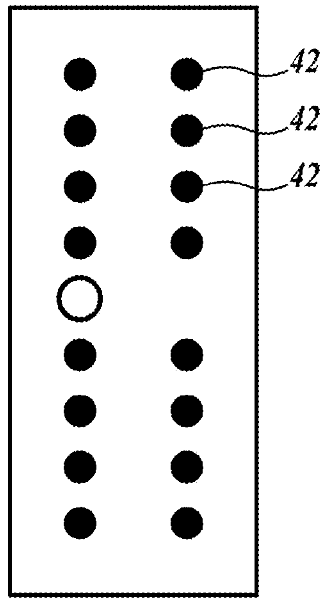
FIG. 2D illustrates electrodes of an implant for delivery of the stimulus in accordance with an embodiment of the present technology.

FIGS. 2A-2D illustrate placement of an implant for delivery of the stimulus in accordance with an embodiment of the present technology. In some embodiments, the implant 40 includes a 16-channel array of micro-wires 42 (also referred to as electrodes). These micro-wires 42 may be implanted into sensorimotor cortex 16 (also referred to as implantation area) of the test animal skull 12 using skull screws 14. In some embodiments, as illustrated in FIGS. 2C and 2D, an 8×2 tungsten micro-wire array was soldered to a custom printed-circuit-board (PCB) with mating connector (e.g., DF30 connector) to the vias placed on the bottom of the PCB. Each micro-wire was 30 μm in diameter covered with 5 μm thick insulation. In some embodiments, the rows were 1.2 mm apart, while the pitch between each electrode in a row was 400 μm. In other embodiments, other dimensions, materials and numbers of micro-wires are also possible.

In some embodiments, the implant 40 was lowered using a stereotaxic manipulator within the cranial window to 1.5 mm depth. Ground wires were wrapped around several skull screws 14. The array was secured in place using 2-part dental acrylic (e.g., C.B. Metabond), exposing the DF-30 connector on top of the array for attachment to cables for delivering stimulation signals to and recording from each electrode.

In some embodiments, in each animal, a stimulation site was chosen corresponding to sensory activity related to the left forepaw, which is the limb used to control the joystick. The activation of both sensory and motor areas was measured prior to selecting the electrode for each experiment to confirm that the stimulation site did not trigger muscle activity or movement.

Figure 3:
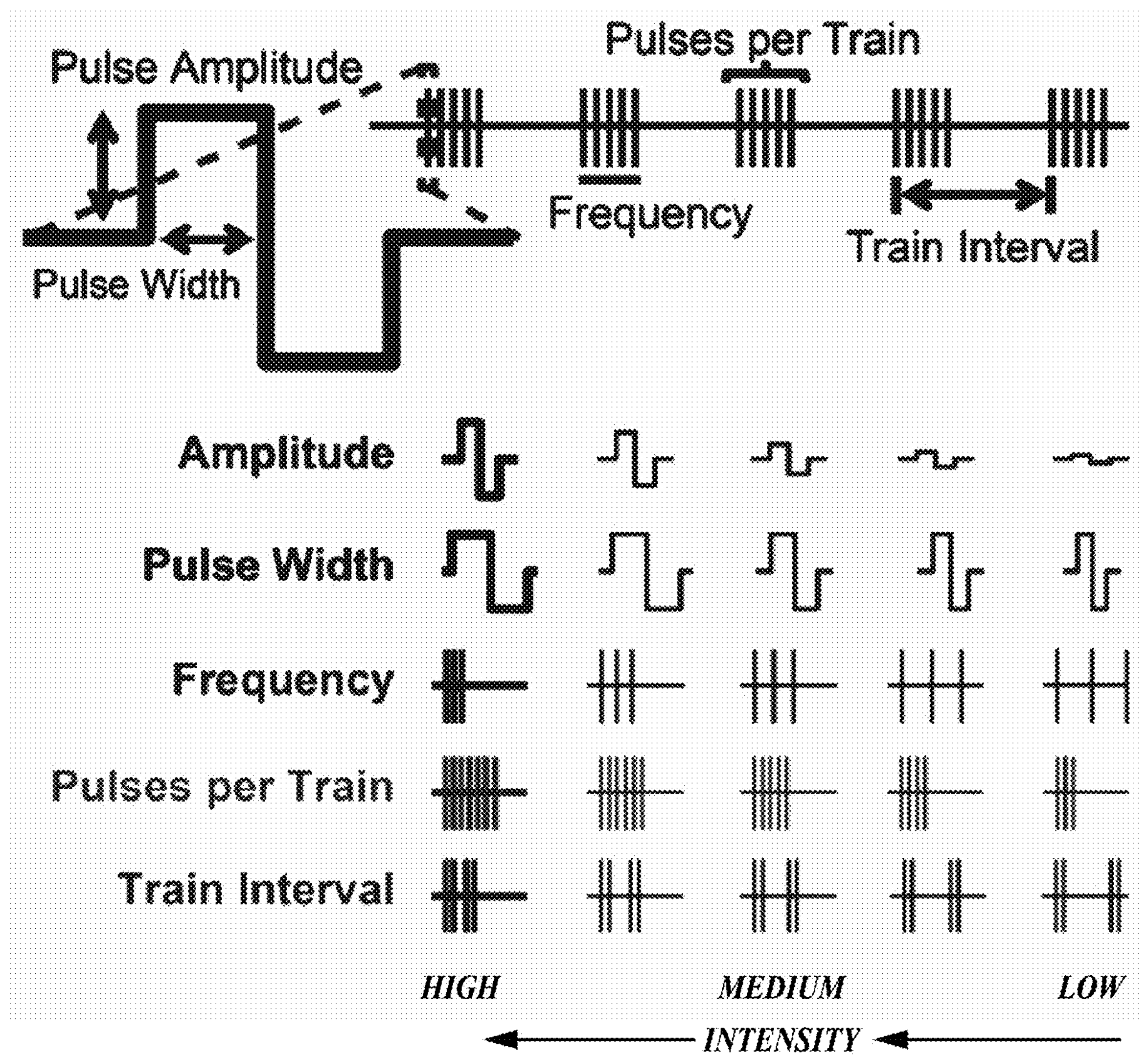
FIG. 3 is a graph illustrating stimulation parameters in accordance with embodiments of the present technology.

FIG. 3 is a graph illustrating stimulation parameters in accordance with embodiments of the present technology. In some embodiments, the stimulation parameters (neural signals) include a set of five features: amplitude, pulse-width, pulse frequency, train interval, and number of pulses. Each parameter can be individually varied around a base pattern. Some non-limiting examples of such base parameters are amplitude of 70 μA, pulse-width of 200 ms, train interval of 100 ms, pulse frequency of 300 Hz, and five pulses per train. The intensity of the illustrated stimulation parameters is qualitatively marked as high, medium and low. In other embodiments, other stimulation parameters with their corresponding base values are also possible. These stimulation parameters (neural signals) define information transferred to the brain, spinal cord or peripheral nerves as electrical stimulus. The neural signals (e.g., cortical signals) are evoked via an electrical stimulus delivered through the implant electrodes.

In different embodiments, the ranges of each of these parameters are selected for both safety and ability to recruit cortical neural populations. Amplitude defines the height of each pulse, within a range of, for example, 5-120 μA or 0-120 μA. Pulse-width defines the width of each pulse, within a range of, for example, 50-500 μs. Frequency defines the rate of each stimulus pulse within a train, within a range of, for example, 50-400 Hz or 1-400 Hz in different embodiments. Pulse per train defines the length of a stimulation train within a range of, for example, 5-20 or 1-20 pulses per train. Train interval defines the time between the start of consecutive stimulation trains within a range of, for example, 50-400 ms or 50-500 ms. In other embodiments, other ranges of parameters are also possible.

In some embodiments, the stimulation pulses are biphasic, symmetrical, and constant-current to prevent any charge build-up around the electrode tip from damaging the surrounding tissue. Electrical current may be delivered through the selected electrode and a common reference wire, consistent with a bi-polar stimulation protocol. The anodic phase may be first delivered through the selected electrode. Since both electrodes have similar impedance, this definition of electrodes is somewhat arbitrary.

Figure 4B:
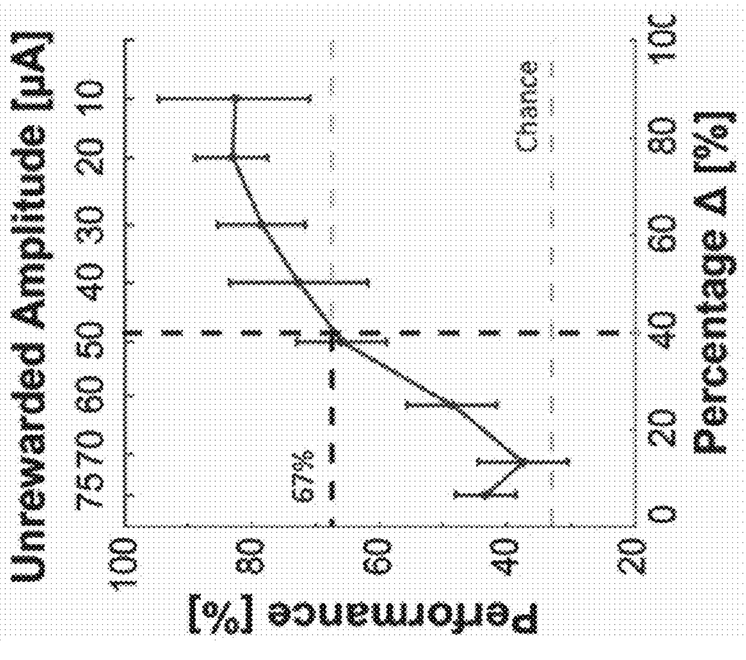
FIG. 4B is a graph illustrating discriminability of the stimulation parameters in accordance with embodiments of the present technology.
Figure 4A:
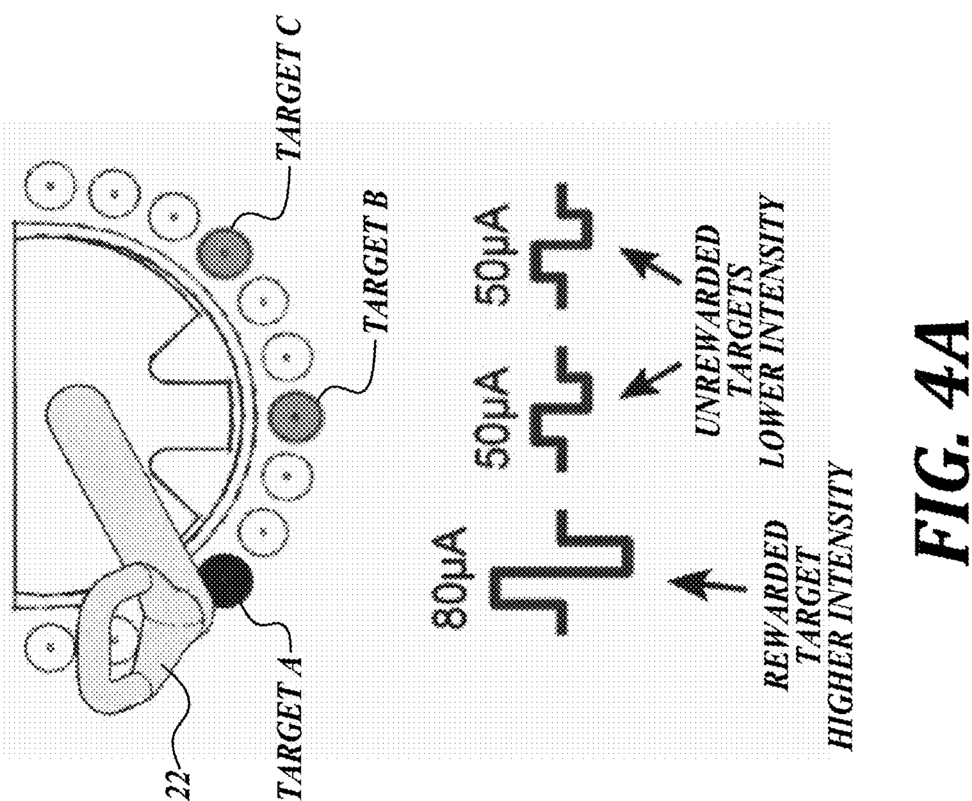
FIG. 4A illustrates a three-alternative forced choice (3AFC) in accordance with an embodiment of the present technology.

FIG. 4A illustrates a three-alternative forced choice (3AFC) in accordance with an embodiment of the present technology. The illustrated experimental setup includes three targets, with only one target (e.g., target A) being rewarded (e.g., by drops of apple juice). For example, when the test animal positions the manipulator into a rewarded target, a higher intensity of the stimulation signal (i.e., the rewarded intensity of the stimulation signal) is administered. Therefore, when entering a target, stimulation pattern is delivered as a feedback that indicates a rewarded or "correct" choice. If the test animal keeps the manipulator in that target for a period of time (e.g., 1.25 s), the animal is rewarded. If the test animal places the manipulator to an unrewarded target (e.g., targets B or C), a lower intensity of the stimulation signal (i.e., the unrewarded intensity of the stimulation signal) is administered. Generally, the test animals are quick learners and they want to get rewarded. Therefore, a limiting factor for a better performance of the test animal is a cortical recognition and discrimination at to whether the stimulation intensity is of the rewarded type.

FIG. 4B is a graph illustrating discriminability of the stimulation parameters in accordance with embodiments of the present technology. The horizontal axis indicates a percentage change between the highest amplitude of the applied stimulus signal and the amplitude of a given signal. The vertical axis indicates the performance of the animal. For example, for a randomized three-alternative choice a chance for randomly arriving to a correct answer is 33%. To reliably compare the resolution of each parameter, the Just-Noticeable-Difference (JNDs) was explicitly measured. The JND measurement is the magnitude of change required for the animal to detect a difference between two signals. By using this method to determine resolution of a signal, each pattern was modulated until the animal could reliably discriminate between rewarded and unrewarded patterns.

For simplicity, in most embodiments the rewarded pattern was nominally a "higher intensity" pattern, corresponding to higher amplitude, longer pulse-width, shorter train intervals, higher number of pulses per train, and/or higher frequency. Conversely, the unrewarded patterns were of the "lower intensity." In other embodiments, the inverse scenario may be possible, that is the rewarded patterns being of the "lower intensity."

In the example illustrated in FIG. 4B, the JND or the difference between the rewarded amplitude and the unrewarded amplitude is 30 μA or a 40% change (bottom x-axis). The target location of the two unrewarded and the single rewarded pattern (as illustrated in FIG. 4A above) were randomized for each trial. The sensory threshold is nominally halfway between chance (33%) and 100%, resulting in a threshold of 67%.

In some embodiments, a two-choice task may suffice for the tests. However, the three-choice task may be preferable given the tendency for the test animals to repeatedly visit only one target. To encourage a more random search strategy, a 20-trial history negatively biased the selection of the location of the reward target from targets where the animal successfully accomplished the task previously. In some embodiments, this adaptive algorithm prevents repetitive movements of the manipulator to a single target location.

Several JND measurements were collected to measure the resolution at the low, middle and high values of each parameter range. Since each parameter has a different magnitude from min to max value, and in order to directly compare paradigms, each parameter range is normalized as a function of percent change. For example, if the rewarded value was 80 μA, and the unrewarded value was 30 μA, normalization would set the percentage difference at 62.5%. For the example shown in FIG. 4B, when the difference between rewarded parameter and unrewarded parameter is greater than about 30 μA (e.g., from about 80 μA to about 50 μA), the test animal was able to correctly identify the higher value parameter more than 67% of the time.

Figure 5A:
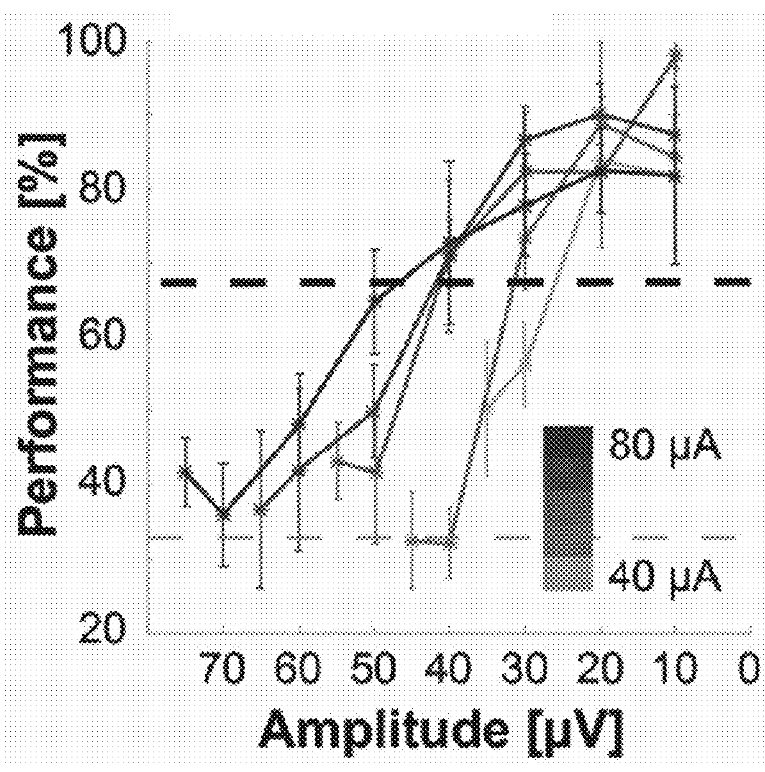
FIGS. 5A-5F are graphs illustrating sensitivity to the stimulation parameters in accordance with embodiments of the present technology.
Figure 5B:
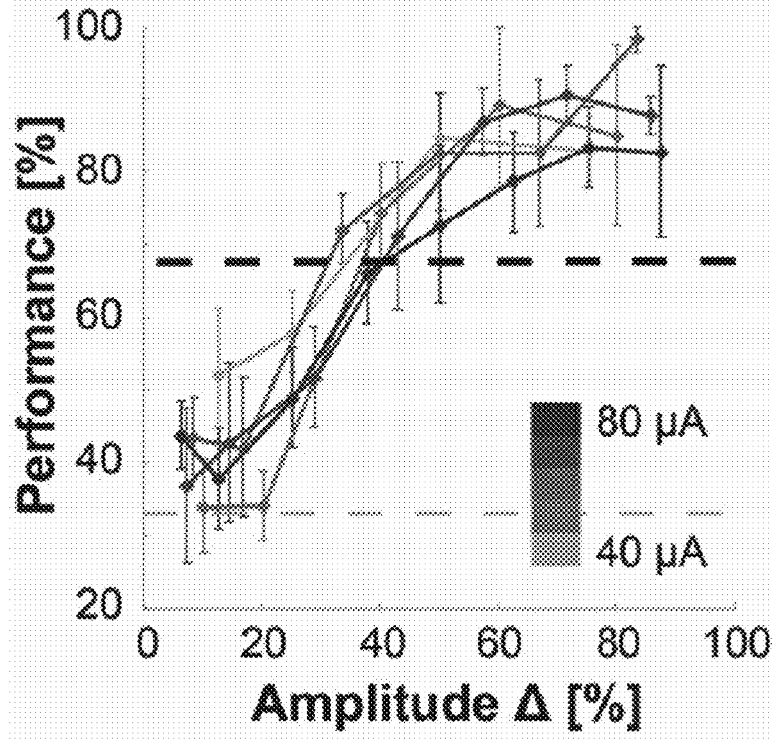
Figure 5C:
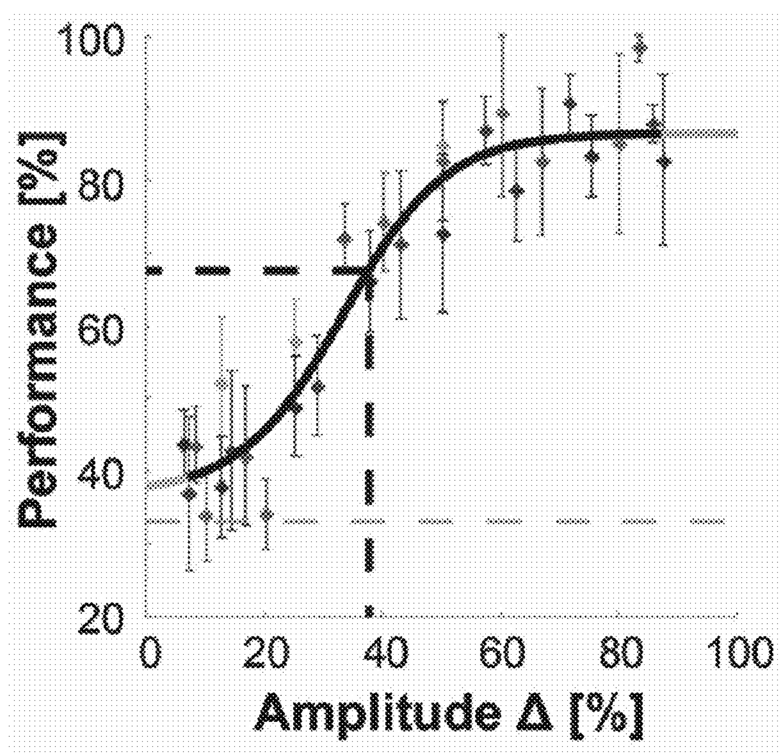
Figure 5D:
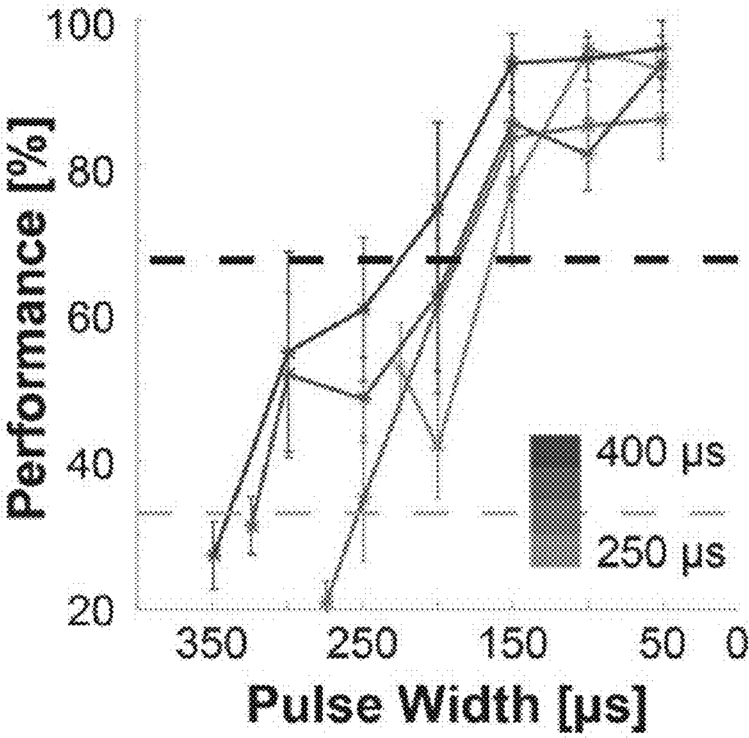
Figure 5E:
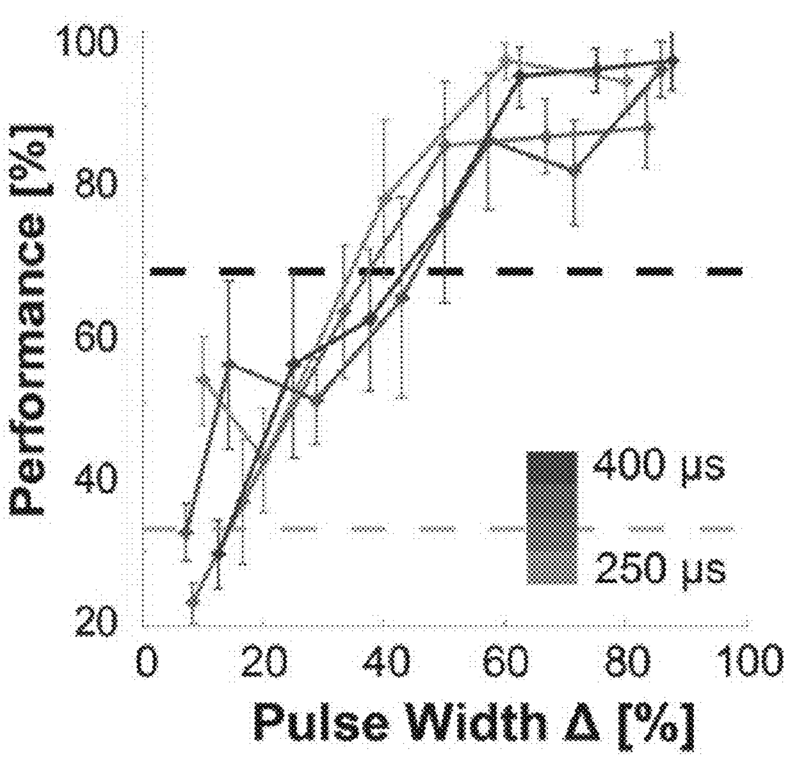
Figure 5F:
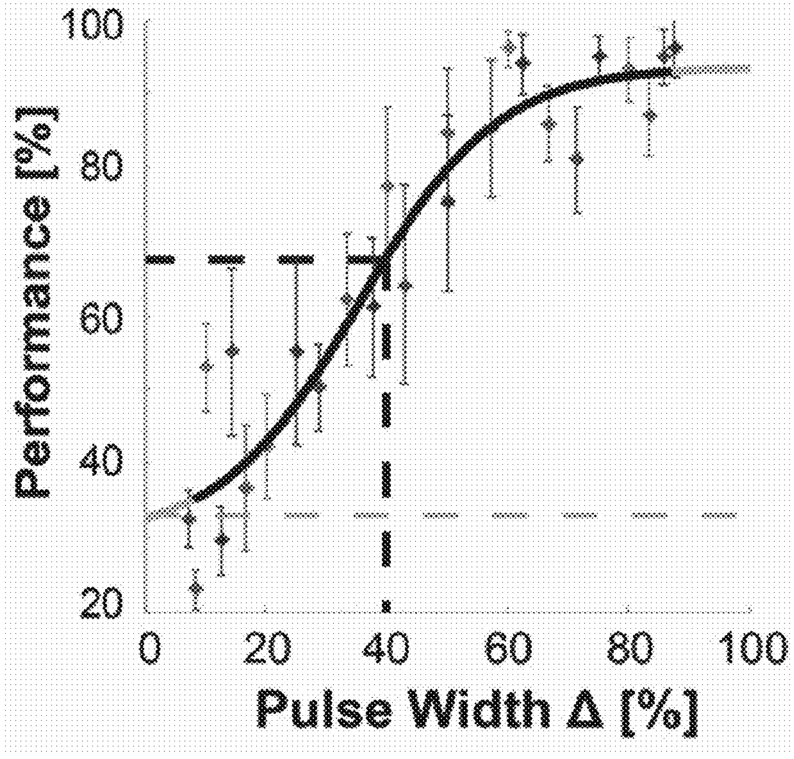

FIGS. 5A-5F are graphs illustrating sensitivity to the stimulation parameters in accordance with embodiments of the present technology. The vertical axes in all graphs show performance discrimination for the test animals that received cortical stimulation signals. FIGS. 5A-5C illustrate scenarios where the amplitude of the cortical stimulation signals was varied. FIGS. 5D-5F illustrate scenarios where the pulse-width of the cortical (neural) stimulation signals was varied. A range of 50-100 trials were collected for each individual data point. Vertical lines indicate error bars.

FIGS. 5A and 5D each show psychometric curves capturing performance of discrimination between the rewarded "high intensity" pattern (shown in the legend) vs. the unrewarded value (plotted on the x-axis). FIG. 5A corresponds to amplitude, and FIG. 5D corresponds to pulse-width as the stimulation parameter. The individual psychometric curves were measured throughout the perceivable range of stimulus amplitude. In FIGS. 5A and 5D, five curves were collected when the rewarded intensity value was fixed. In FIGS. 5B and 5E, the same results are normalized to the percentage difference between the rewarded amplitude value and the unrewarded amplitude value. In FIGS. 5C and 5F, the data from the corresponding preceding Figures are used to fit a sigmoidal curve. Such psychometric curves as in FIGS. 5C and 5F are calculated individually for each animal, FIG. 5C again corresponds to amplitude as the stimulation parameter, and FIG. 5F corresponds to pulse-width as the stimulation parameter. The JND measurement is calculated as the point where this sigmoidal curve crosses the sensory threshold that is 67%. The JND measurement, calculated as percentage change required to cross the sensory threshold (67%), was used to compare sensitivity across parameters and across animals. The normalized JND measurement can also be called a Weber Fraction.

FIGS. 6A-6F are graphs illustrating just-noticeable-differences (JND) for the stimulation parameters in accordance with embodiments of the present technology. The JND is illustrated for a variety of stimulation encoding parameters, collectively quantifying perceptual resolution across the stimulation parameter space. During the experiments, the intensity of a single stimulation parameter was modulated, while all other parameters were fixed at perceivable values. The averages are plotted for a group of test animals (typically 5-8 animals in a group) for each stimulation parameter.

To capture JND resolution across the entire range of perceivable intensities, the discriminability is equated with performance. By measuring each animal's ability to discriminate between a high intensity sensation vs. a lower intensity sensation, perceptual resolution is determined for each parameter.

Figure 6A:
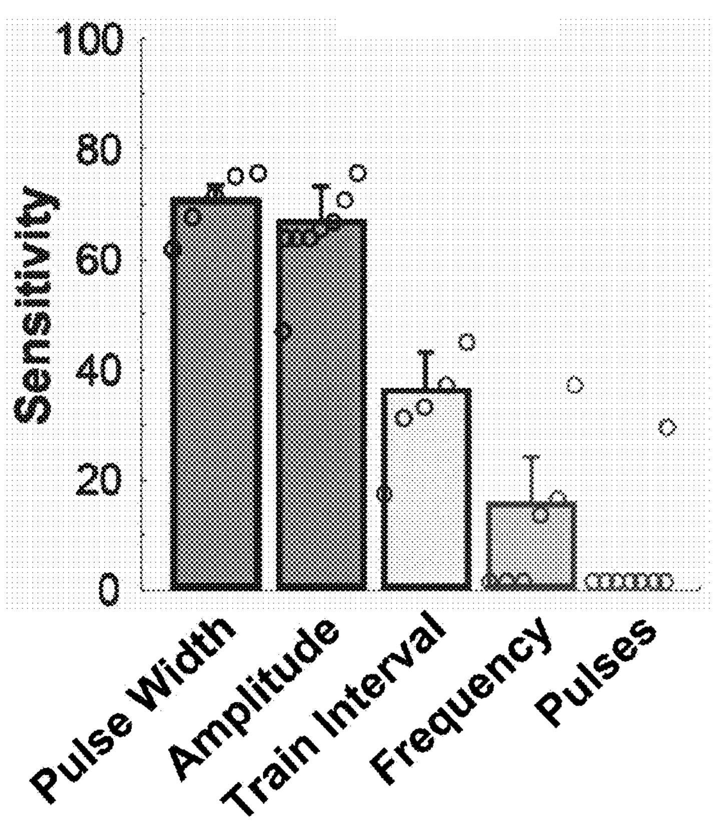
FIGS. 6A-6F are graphs illustrating just-noticeable-differences (JND) for the stimulation parameters in accordance with embodiments of the present technology.
Figure 6B:
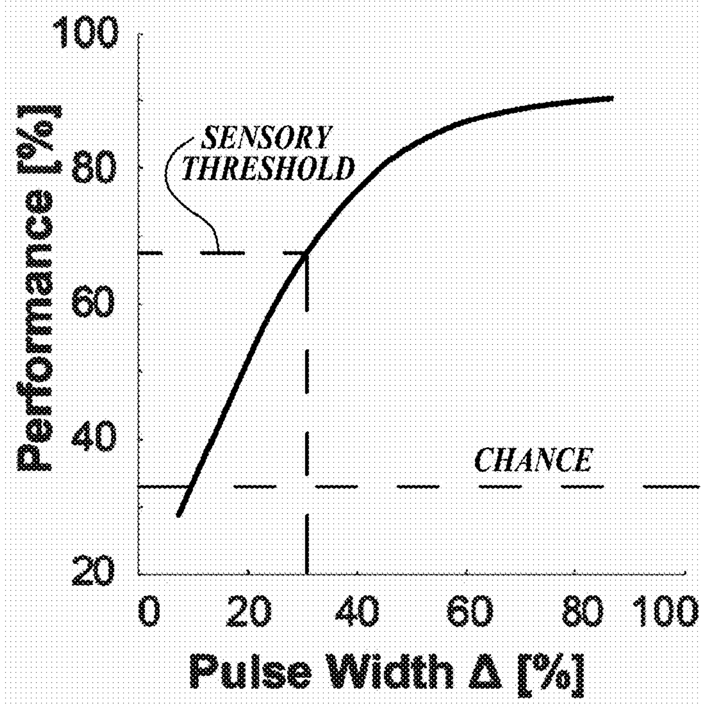
Figure 6C:
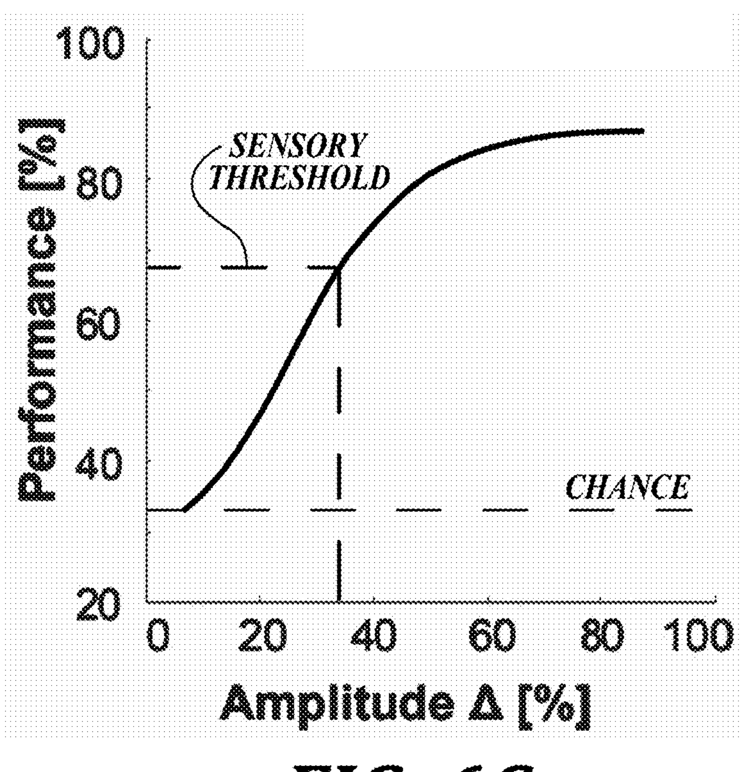

FIG. 6A shows sensitivity of each parameter that is calculated as the inverse of the just-noticeable difference across all animals. The highest resolution parameters pulse-width and amplitude measured JND of about 30% and about 34%, respectively (as shown in FIGS. 6B and 6C). For the examples shown in FIGS. 6B and 6C, about 30% change in either parameter is required for the animal to reliably recognize two patterns as being distinct. This corresponds to a sensitivity of about 70% (FIG. 6A), which is the lowest single parameter JND's measured. For both amplitude and pulse-width stimulations, each of the individual psychometric curves overlap when normalized.

Figure 6D:
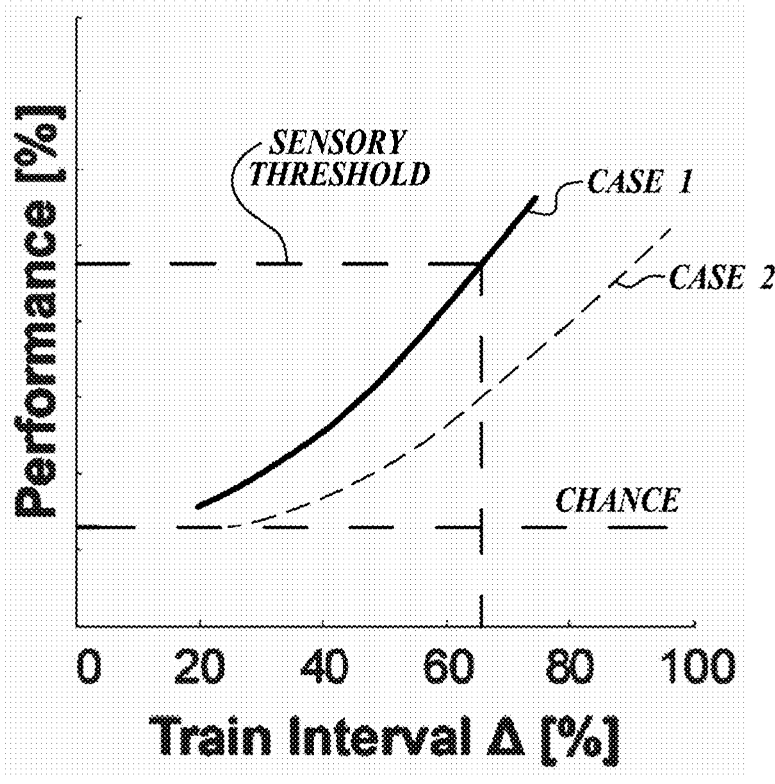

FIG. 6D illustrates measurements of resolution for train interval that indicates relatively moderate, but consistent, sensitivity. The measured JND (case 1, solid line) was about 65%. This corresponds to a 35% sensitivity for train interval. Animal's JND discriminating was also measured and shown as case 2, dashed line in FIG. 6D. For case 2, the stimulation pulses were delivered continuously, or pulses were delivered grouped into trains (as explained with reference to FIG. 3 above). This experiment showed pulse trains occurring at a rate of faster than 100 ms per train being perceived as a tonic, continuous stimulation, thus setting a lower frequency bound for perception of distinct pulse trains. Therefore, modulation of train interval may be a reliable way to modulate intensity. However, there may only be a few discriminable steps possible between the maximum and minimum of the tested range.

Figure 6E:
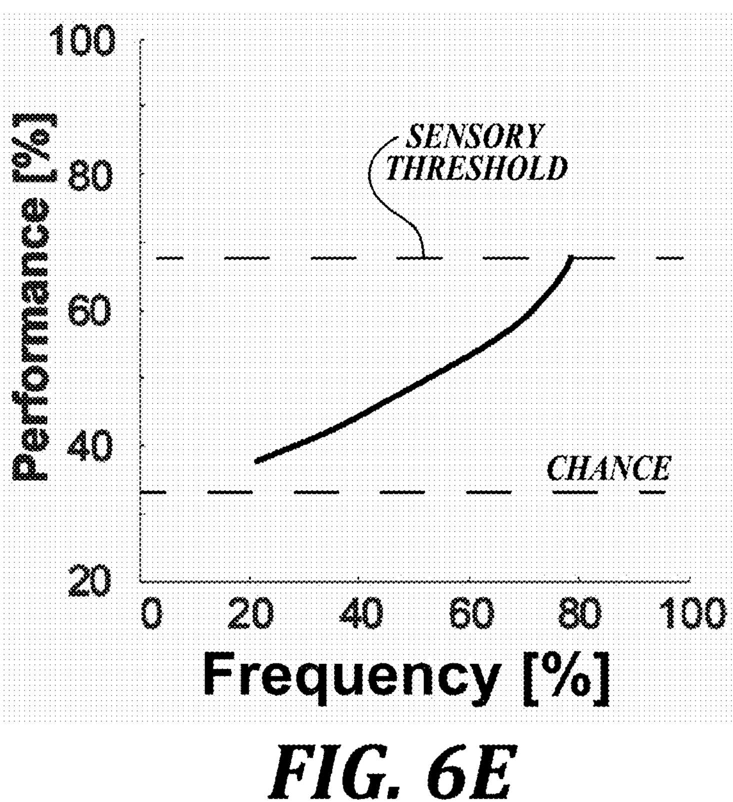

FIG. 6E illustrates the stimulation parameter being a frequency, resulting in JND of about 86%. In particular, three of six animals tested were unable to discriminate between even the highest (400 Hz) and lowest (50 Hz) values of our range. Even the best performing animal had only moderate success at frequency discrimination, requiring a 60% change in frequency to discriminate different stimulus trains. The only discriminable frequency pairs occurred when the lower frequency was below 100 Hz. Therefore, lower frequencies may be discriminable (e.g., frequencies below 100 Hz), but performance of the test animal declines when higher frequencies are used.

Figure 6F:
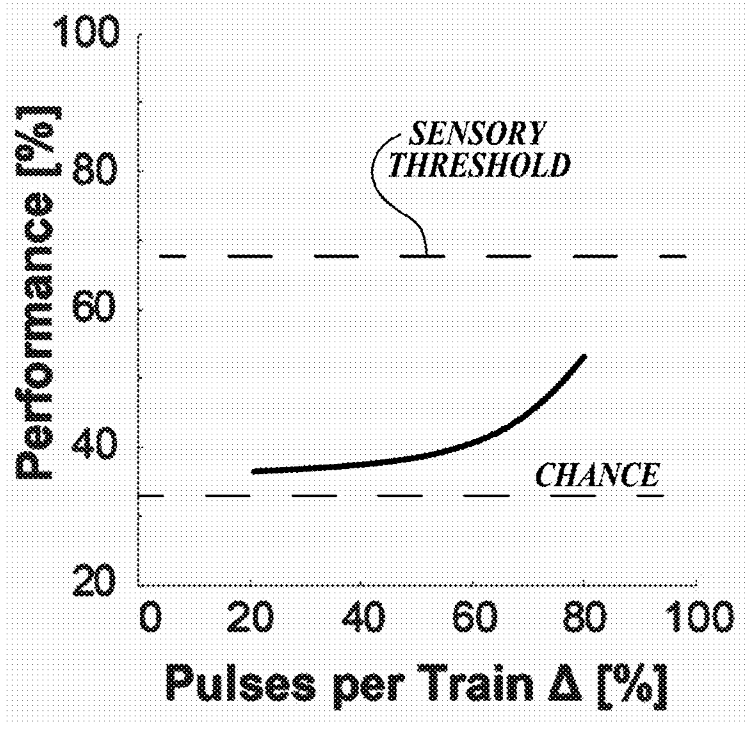

FIG. 6F illustrates modulation of the parameter pulses-per-train (PPT). This stimulation parameter yields little perceptible change. For example, six of seven animals could not discriminate between the highest (20 pulses) and lowest (5 pulses) number of pulses. Since most animals were unable to discriminate between the maximum and minimum values of PPT, the experimental paradigm was flipped to test if the lower value was perceived differently. That is, the animal was rewarded for locating the lowest intensity sensation (5 pulses per train) and discriminating between several higher unrewarded conditions of 10, 12, 15, and 20 pulses per train. Only one animal was able to succeed for a single pair of stimuli (5 vs. 20 pulses per train).

As shown in FIG. 6A, pulse-width and amplitude provided the greatest sensitivity and allow animals to better discriminate between the rewarded intensity and the unrewarded intensities. Temporal parameters such as train interval, frequency, and pulses per train provided relatively lower sensitivity during direct brain stimulation (or spinal cord or peripheral nerves stimulation). In at least some embodiments, pulse-width and amplitude therefore enable the highest resolution encoding scheme.

Figure 7:
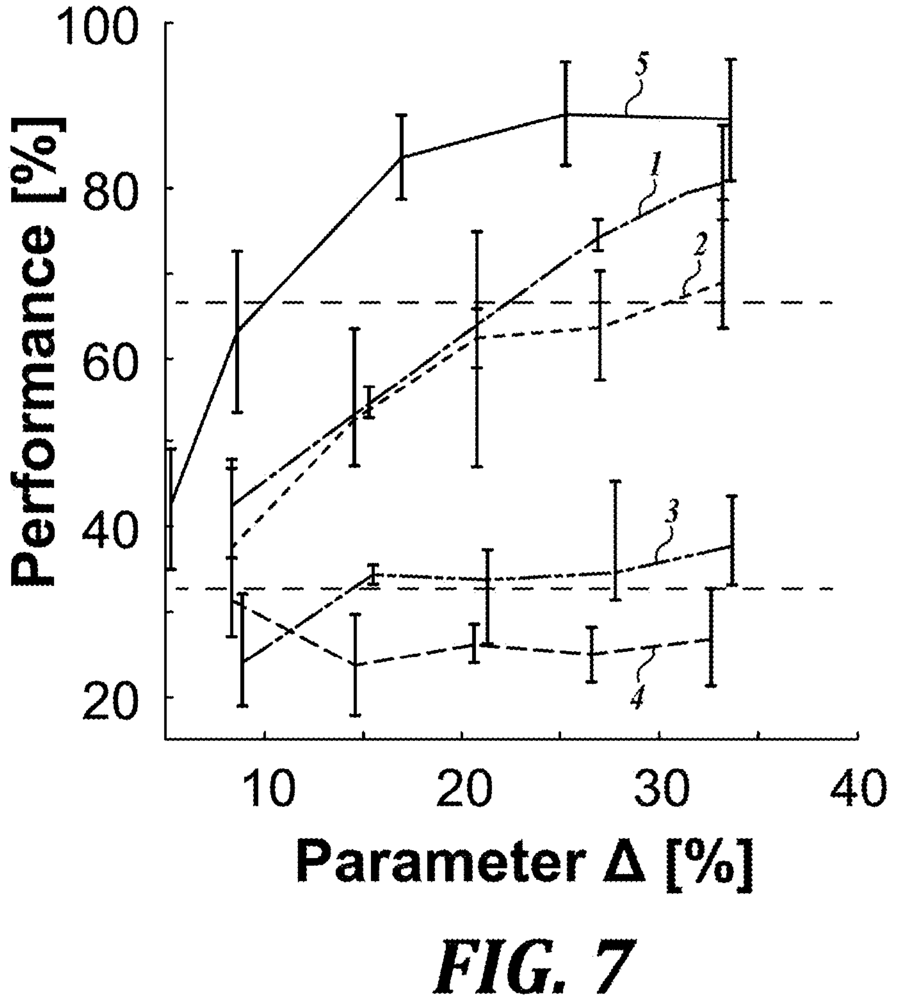
FIG. 7 is a graph illustrating discriminability of the stimulation parameters in accordance with embodiments of the present technology.

FIG. 7 is a graph illustrating discriminability of the stimulation parameters in accordance with embodiments of the present technology. Analogously to FIGS. 6B-6F above, the horizontal axis indicates change in parameter values, and the vertical axis indicates performance percentage. Statistical experimental errors are indicated by vertical bars. The two horizontal dash lines indicate performance thresholds of 33% and 67%. Data was acquired over several thousand trials using 4-5 subjects (test animals) for each stimulation parameter. The particular stimulation parameters shown in FIG. 7 are marked by numerals 1-5 as follows:

1—amplitude;
2—pulse-width;
3—concurrently modulating amplitude negatively and pulse-width positively;
4—concurrently modulating pulse-width negatively and amplitude positively; and
5—concurrently modulating both the amplitude and pulse-width positively.

Collectively, the results shown in FIG. 7 illustrate the effects of charge per pulse (CPP) by varying amplitude and pulse-width, either individually or concurrently. For example, increasing the amplitude or increasing the pulse-width of an electrical signal from given baseline signal amplitude or pulse-width in turn increases CPP. Such increase in CPP causes an increased performance of the test animal, as indicated by curves 1 (amplitude) and 2 (pulse-width).

Conversely, combining a higher amplitude with a smaller pulse-width or the other way round, as indicated by curves 3 and 4, may result in a little change in overall CPP even if one of the stimulation parameters (either amplitude or pulse-width) is increasing, because of the corresponding decrease in the other parameter (either pulse-width or amplitude). In some embodiments, a product of the pulse-width and amplitude was set to a constant value (e.g., 16 nC). Such general "flatness" of the CPP results in a generally flat animal performance over the range of parameter delta changes, indicated by the test animal no longer being capable to appreciably discriminate within the test range of encoded values.

Finally, when both the amplitude and pulse-width of the signal are increased, as shown in curve 5, the CPP increases faster with the parameter delta changes. As a result, performance of test animals increases faster. For example, the 67% threshold is reached at about 11% parameter delta change. Furthermore, an asymptotic performance of about 85% is reached at about 25% parameter delta change. In at least the illustrated embodiments, such performance is significantly improved than when varying just one parameter. For example, for the pulse-width the 67% threshold is reached at about 30% delta change and for the amplitude the 67% threshold is reached at about 34% amplitude delta changes.

In some embodiments, individual weighting function (also referred to as weighting factor) may be assigned to at least two stimulation parameters, for example amplitude and pulse-width. For example, the amplitude may be assigned a weighting function of 0.6 and the pulse-width may be assigned a weighting function of 0.4. As another non-limiting example, the amplitude may be assigned a weighting function of 0.45, the pulse-width may be assigned a weighting function of 0.35, and the frequency may be assigned a weighting function of 0.2. A person of ordinary skill will understand that other combinations of stimulation parameters and their corresponding weighting functions are also possible.

In some embodiments, a combination of stimulation parameters may include one combination of the pulse-width and the amplitude sent to the user in a first stimulus train, and another combination of the pulse-width and the amplitude sent to the user in a second stimulus train. The first combination may be different from the second combination. In some embodiments, the first stimulus train is separated from the second stimulus train by a time gap, for example, a time gap that is shorter than 50 ms or 100 ms. Without being bound to theory, it is believed that sending the stimulation in time-separated trains may result in improved sensitivity (and hence improved bandwidth) of the stimulation sent to the cortex. Different stimulus trains may be separated by a duration of time that depends on the duration of the stimulus train itself. For example, the first stimulus train may be separated from the second stimulus train by a time gap that is shorter than a 25%, 50% or 75% of the first stimulus train.

As explained above, other parameters (i.e., temporal parameters such as train interval, frequency, and pulses per train) are characterized by a lower sensitivity during direct brain stimulation. However, these temporal parameters may also be useful for modulating the stimulation in different embodiments.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Such computers, controllers and data processors may include a non-transitory computer-readable medium with executable instructions. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Where methods are described, the methods may include more, fewer, or other steps. Additionally, steps may be performed in any suitable order. Accordingly, the disclosure can encompass other embodiments not expressly shown or described herein. In the context of this disclosure, the term "about" means+/−5% of the stated value.

For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

What is claimed is:

1. A system for delivering information to a user, comprising:

an implant electrically coupled to a brain, a spinal cord or peripheral nerves of the user through implant electrodes, wherein the implant is configured to deliver electrical stimulus through the implant electrodes, wherein the electrical stimulus conveys somatosensory information to the user, wherein the user is aware of the somatosensory information being conveyed, and wherein the somatosensory information evokes a limb perception of a functioning limb, and wherein the limb perception is sensed by the user being aware of the somatosensory information being conveyed and capable of interpreting the somatosensory information being conveyed;

a computing device comprising a non-transitory computer-readable medium, wherein the computer-readable medium includes computer-executable instructions stored thereon which, in response to execution by at least one processor of the computing device, cause the computing device to perform actions comprising:

delivering a first electrical stimulus via the implant electrodes, wherein the first electrical stimulus evokes neural signals, wherein the neural signals correspond to information transferred to the brain, spinal cord or peripheral nerves through the implant electrodes, and wherein the first electrical stimulus is encoded as a combination of a pulse-width and an amplitude, detecting user's response to the first electrical stimulus; and based on detecting user's response, determining a second electrical stimulus, wherein a second intensity of the second electrical stimulus differs from a first intensity of the first electrical stimulus, and wherein the first electrical stimulus and the second electrical stimulus are perceivable to the user having the implant;

wherein both the pulse-width and the amplitude of each of the first electrical stimulus and the second electrical stimulus are concurrently varied to produce a variable charge-per-pulse (CPP) at the implant electrodes.

2. The system of claim 1, wherein the combination further comprises a frequency.

3. The system of claim 2, wherein the frequency is within a range of 1-400 Hz.

4. The system of claim 1, wherein the amplitude is less than 120 μA.

5. The system of claim 1, wherein the pulse-width is within a range of 50-500 μs.

6. The system of claim 1, wherein a number of pulses in a train of pulses of the first electrical stimulus or the second electrical stimulus is within a range of 1-20 pulses per train, and a train interval is within a range of 50-500 ms.

7. The system of claim 1, wherein determining the second electrical stimulus is based on detecting a Just-Noticeable-Difference (JND) between user's response to the first electrical stimulus and the second electrical stimulus.

8. A method for stimulating a user, comprising:

delivering a first electrical stimulus via electrodes connecting an implant to a brain, a spinal cord, or peripheral nerves of the user, wherein the electrical stimulus conveys somatosensory information to the user, wherein the user is aware of the somatosensory information being conveyed, and wherein the somatosensory information evokes a limb perception of a functioning limb, and wherein the limb perception is sensed by the user being aware of the somatosensory information being conveyed and capable of interpreting the somatosensory information being conveyed; and based on delivering the first electrical stimulus, evoking neural signals in the brain, spinal cord, or peripheral nerves of the user, detecting user's response to the first electrical stimulus; and based on detecting user's response, determining a second electrical stimulus, wherein a second intensity of the second electrical stimulus differs from a first intensity of the first electrical stimulus, and wherein the first electrical stimulus and the second electrical stimulus are perceivable to the user having the implant;

wherein each of the first electrical stimulus and the second electrical stimulus encodes the neural signals via a combination of a pulse-width and an amplitude, wherein both the pulse-width and the amplitude are concurrently varied to produce a variable charge-per-pulse (CPP) at the implant electrodes.

9. The method of claim 8, wherein the neural signals correspond to information transferred to the user.

10. The method of claim 9, further comprising measuring information delivered to the user.

11. The method of claim 9, wherein the amplitude of the combination remains constant and the pulse-width of the combination changes to modulate the neural signal.

12. The method of claim 9, wherein the pulse-width of the combination remains constant and the amplitude of the combination changes to modulate the neural signal.

13. The method of claim 8, wherein determining the second electrical stimulus is based on detecting a Just- Noticeable-Difference (JND) between user's response to the first electrical stimulus and the second electrical stimulus.

14. A method for delivering electrical stimulus through an implant having implantable electrodes coupled to a brain, or a spinal cord, or peripheral nerves of a user, comprising:

delivering a first electrical stimulus to the user via the implantable electrodes, wherein the electrical stimulus conveys somatosensory information to the user, wherein the user is aware of the somatosensory information being conveyed, and wherein the somatosensory information evokes a limb perception of a functioning limb, and wherein the limb perception is sensed by the user being aware of the somatosensory information being conveyed and capable of interpreting the somatosensory information being conveyed, wherein the first electrical stimulus is encoded as a combination of a pulse-width and an amplitude, wherein both the pulse-width and the amplitude of the first electrical stimulus are concurrently varied to produce a variable charge-per-pulse (CPP) at the implant electrodes;

based on delivering the first electrical stimulus, evoking neural signals in the brain, the spinal cord, or the peripheral nerves of the user;

detecting user's response to the first electrical stimulus; and based on detecting patient's response, determining a second electrical stimulus that is different than the first electrical stimulus, wherein both the pulse-width and the amplitude of the second electrical stimulus are concurrently varied, wherein a second intensity of the second electrical stimulus differs from a first intensity of the first electrical stimulus, and wherein the first electrical stimulus and the second electrical stimulus are perceivable to the user having the implant.

15. The method of claim 14, further comprising:

assigning individual weighting functions to initial values of the pulse-width and the amplitude of the electrical stimulus of the first electrical stimulus, such that final values of the pulse-width and the amplitude of the second electrical stimulus are based on adjusting the initial values of the pulse-width and the amplitude of the first electrical stimulus with the individual weighting functions for the pulse-width and the amplitude of the second electrical stimulus.

16. The method of claim 14, wherein the combination comprises a first combination of the pulse-width and the amplitude sent to the user in a first stimulus train of the first electrical stimulus, and a second combination of the pulse-width and the amplitude sent to the user in a second stimulus train of the first electrical stimulus, wherein the first combination is different from the second combination, and wherein the first stimulus train is separated from the second stimulus train by a time gap that is shorter than 100 ms.

17. The method of claim 16, wherein the time gap is shorter than 50 ms.

18. The method of claim 14, wherein the combination comprises a first combination of the pulse-width and the amplitude sent to the user in a first stimulus train of the first electrical stimulus, and a second combination of the pulse-width and the amplitude sent to the user in a second stimulus train of the first electrical stimulus, wherein the first combination is different from the second combination, and wherein the first stimulus train is separated from the second stimulus train by a time gap that is shorter than a 50% of the first stimulus train.

19. The method of claim 14, wherein determining the second electrical stimulus is based on detecting a Just-Noticeable-Difference (JND) between user's response to the first electrical stimulus and the second electrical stimulus.

* * * * *